United States Patent [19]

Maier

[11] 4,171,969
[45] Oct. 23, 1979

[54] BIS(AMINOMETHYL)PHOSPHINIC ACID

[75] Inventor: Ludwig Maier, Arlesheim, Switzerland

[73] Assignee: Ciba-Geigy Corporation, Ardsley, N.Y.

[21] Appl. No.: 875,842

[22] Filed: Feb. 7, 1978

[30] Foreign Application Priority Data

Feb. 10, 1977 [CH] Switzerland .................. 1614/77

[51] Int. Cl.² .................. C07F 9/30; A01H 3/04; A01N 5/00
[52] U.S. Cl. .................. 71/86; 260/501.12; 260/502.5
[58] Field of Search .................. 260/502.5, 501.12; 71/86

[56] References Cited

U.S. PATENT DOCUMENTS 3,160,632  12/1964  Toy et al. .................. 260/502.5
3,894,861  7/1975  Hartman .................. 71/86

OTHER PUBLICATIONS

Il'ina et al., "Izv. Akad. Nauk. SSSR", vol. 8, 1968, pp. 1860 to 1862, English Translation Pagination, pp. 1759 to 1761.

*Primary Examiner*—Joseph E. Evans
*Attorney, Agent, or Firm*—Harry Falber; Frederick H. Rabin

[57] ABSTRACT

Method for synthetizing bis(aminomethyl)phosphinic acid and its salts are disclosed. This acid corresponds to the formula

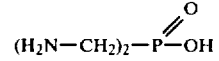

and possesses plant-growth retarding activity.

4 Claims, No Drawings

BIS(AMINOMETHYL)PHOSPHINIC ACID

The present invention relates to a process for the production of a new phosphinic acid and the salts thereof. The bis(aminomethyl)phosphinic acid has the formula

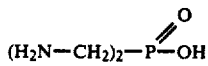

and has a plant growth-regulating, especially inhibiting, action.

On account of its amphoteric character, this acid is able to form both acid addition salts with strong mineral acids, such HCl, HBr, etc., and salts with bases, such as ammonium and metals salts of alkali metals and alkaline earth metals (Li, Na, K, Ca, Mg), and also of other metals, for example Fe, etc., and salts of amines.

The present invention also relates to these salts and their production, as well as to the use of the new acid and its salts as active ingredients of herbicidal and plant growth-regulating compositions and as starting materials for the production of derivatives and other phosphorus-containing compounds, for example of the polyamide series.

The production of the new phosphinic acid and the salts thereof is carried out by two processes. The first process is based on a catalytic debenzylation of a salt of bis(benzylaminomethyl)phosphinic acid of the formula

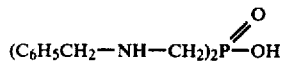

by treating an acid addition salt of (II) in a solvent catalytically with hydrogen. Suitable solvents are water, water/ethanol, but especially glacial acetic acid or acetic acid (in water). A suitable catalyst is palladium (5%) on carbon, and platinum oxide or platinum/carbon. The hydrogenation is carried out under normal pressure and at a temperature between 10° and 50° C., preferably between 20° and 35° C.

The hydrogen uptake of (II) proceeds stepwise, and under specific conditions it is possible to isolate the monobenzylated intermediate. The reaction mixture furthermore tends to take up more hydrogen than is necessary for the reaction, the reason being that, after the debenzylation, the resulting toluene is hydrogenated (120% hydrogen uptake instead of 100% of theory).

The second process starts from a salt of a bis(tert-alkylaminomethyl)phosphinic acid containing tertiary alkyl groups of 4 to 12 carbon atoms, especially from the hydrochloride of bis(tert-butylamino-methyl)phosphinic acid

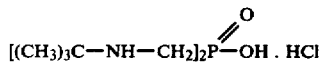

and consists in treating this compound under pressure and at elevated temperature with concentrated hydrobromic acid until the reaction is complete. Preferably this reaction is carried out in a bomb tube under a pressure of up to 40 bar and at a temperature between 150° and 200° C. over a period of about 24 hours and longer.

In this reaction, the tert-butyl groups are split off by the action of HBr in the form of 2 moles of butene,

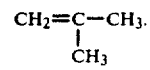

The starting material of the formula (II), bis(benzylaminomethyl)phosphinic acid and salts thereof, as well as bis (alkylaminomethyl) phosphinic acids, have already been described in the literature (M.K. Il'ina and M. Shermergorn, Izv. Akad. Nauk, SSSR, 1968, 1860), but not the specific bis (tert-butylaminomethyl) derivative of the formula (III), which can be prepared in similar manner to the known propyl homologues.

For the production of the starting materials of the formulae II and III, a start is made from bis(hydroxymethyl)phosphinic acid, which is obtained from formaldehyde, hydrochloric acid and $NaH_2PO_2$ or direct by reaction of 50% $H_3PO_2$ with formaldehyde solution and hydrochloric acid under reflux.

The bis(chloromethyl)phosphinic acid

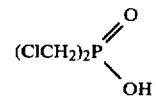

is obtained in simple manner by chlorination of bis(hydroxymethyl)phosphinic acid with $SOCl_2$ via the acid chloride ("Organic Phosphorus Compounds," ed. G. M. Kosolapoff and L. Maier, John Wiley & Sons, New York, 1972).

From this bis(chloromethyl)phosphinic acid and its salts it is possible to prepare the starting materials of the formulae II and III according to the following reaction scheme:

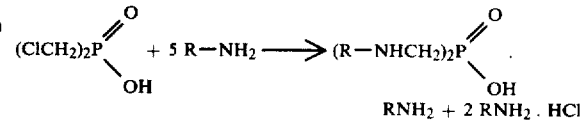

wherein R is either benzyl or tert-butyl.

Accordingly, the benzylamine and tert-butylamine salt of the desired acid (II) and (III) respectively is first formed, which, after acidification for example with HCl, is converted into an acid addition salt.

For the production of the bis(benzylaminomethyl)-phosphinic acid (II) from bis(chloromethyl)phosphinic acid and benzylamine, the benzylamine is used in excess of the stoichiometric amount in order to avoid the formation of resinous products. After distilling off excess benzylamine, acidifying with HCl and recrystallisation, the acid (II) is obtained in the form of the hydrochloride with a melting point of 257-258° C.

The production of bis(tert-butylaminomethyl)phosphinic acid (III), a new compound, proceeds less smoothly, and in the reaction of tert-butylamine with bis(chloromethyl)phosphinic acid it is necessary to carry out the process under pressure at elevated temperature (100°-120° C.). Finally, the desired bis(tert-butylaminomethyl)phosphinic acid (III), the hydrochloride of which melts at 260°-262° C. with decomposition, is obtained by fractional crystallisation.

The new bis(aminomethyl)phosphinic acid obtained according to the process of the invention from the starting materials (II) and (III) is usually in the form of a salt. The hydrochloride is fairly sparingly soluble in glacial acetic acid and precipitates in the preferred method of production, the catalytic debenzylation of (II) in glacial acetic acid. It can then be easily extracted with hot water from the catalyst which is removed by filtration.

The hydrochloride of the bis(aminomethyl)phosphinic acid can be recrystallised from water, water/ethanol or water/acetone and forms white crystals which turn dark at 290° C. and melt with decomposition at 307° C.

The hydrobromide of the new acid melts at 260°–267° C. with decomposition.

The processes of the invention are described in more detail in the following Examples. Example 1 also describes the preparation of known intermediates.

EXAMPLE 1

(a) Bis(hydroxymethyl)phosphinic acid

A mixture of 6.1 kg of a 50% solution of hypophosphorous acid ($H_3PO_2$) in water, 35 liters of conc. hydrochloric acid and 2.9 kg of paraformaldehyde is stirred first at 40°–45° C. until all the ingredients are dissolved, and then heated for 50 hours to reflux. The reaction mixture is then completely concentrated by rotary evaporation and the final remnants of water are removed with toluene by azeotropic distillation. Yield of

5.02 kg (86.2%) of viscous, slightly yellow substance. Instead of $H_3PO_2$, the salt $NaH_2PO_2$ can also be used, as described in the literature [J. Gen. Chem. (USSR) 37, 1768 (1966)].

(b) Bis(chloromethyl)phosphinic acid

With mechanical stirring, 4 kg of

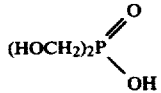

are slowly added to 22.22 kg of thionyl chloride ($SOCl_2$), which is heated to reflux. As a result of the formation of gas (HCl, $SO_2$), the mixture foams strongly at first. When the addition is complete, the reaction mixture is refluxed until the formation of gas has ceased (about 5 hours). After fractionation, the resultant acid chloride ($ClCH_2)_2POCl$ (5 kg=87% of theory) boils at 80°–85° C./0.05–0.1 torr and has a refractive index $n_D^{20}=1.5200$.

With stirring, 2.42 of the above acid chloride are added dropwise to 2 liters of distilled water and the solution is filtered in case some solid has precipitated. The filtrate is concentrated completely by rotary evaporation, affording as residue 2.06 kg (94.5%) of bis(chloromethyl)phosphinic acid with a melting point of 80°–81° C. (white solid).

(c) Hydrochloride of bis(benzylaminomethyl)phosphinic acid (II)

With stirring, 163 g (1 mole) of $(ClCH_2)_2P(O)OH$ are slowly added to 1072 g (1094 ml) of benzylamine. When the strongly exothermic reaction has subsided, the mixture is heated with stirring for 15 hours to 110° C. After cooling, a white precipitate forms. Excess benzylamine is distilled off at about 1 torr and the white residue is then dissolved in 2 liters of distilled water. The solution is filtered and the filtrate is treated with 350 ml of concentrated HCl. After stirring for 2 hours, the white precipitate is collected with suction, washed with water and dried in vacuo at 80° C. Yield: 289 g (84% of theory), m.p.: 253°–254° C. For analysis, a small sample is recrystallised once more from water. Melting point: 257°–258° C.

Analysis: $C_{16}H_{21}N_2O_2P.HCl$(340.79). Found C, 56.2; H, 6.5; N, 8.0; Cl, 10.6; P, 9.2. Calculated C, 56.39; H, 6.51; N, 8.22; Cl, 10.4; P, 9.09.

Titration in $H_2O$ with 0.1N tetramethylammonium hydroxide solution gives 2 potential breaks:

1st break: equiv. wt. : found 339 (calc. 340.7)
2nd break: equiv. wt. : found 171 (calc. 170.3).

The $^1H$ and $^{31}P$-NMR spectra confirm the structure of the compound as

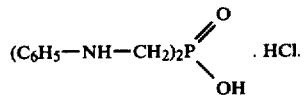

(d) Hydrochloride of bis(aminomethyl)phosphinic acid (1.) 25 g (73 moles) of the hydrochloride obtained in (c) are dissolved in 600 ml of glacial acetic acid and the solution is hydrogenated with 2 g of Pd-C (5%) at 20°–25° C. with hydrogen. After a 19% uptake of hydrogen, a further 2 g of Pd-C (5%) is added and after 54 hours the uptake of hydrogen ceases. Altogether 3.18 liters (97% of theory) of hydrogen are taken up. The catalyst is removed by filtration and the clear, colourless filtrate concentrated by rotary evaporation, affording as residue 2.7 g (14.7%) of white

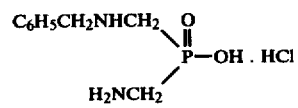

(m.p.: sinters at 270° C. and melts at 278°–281° C. with decomp.).

The catalyst is extracted with water overnight in a Soxhlet extractor. A slightly yellow solution forms. When concentrated in a rotary evaporator, this solution yields 9 g (76.85%) of quite pure, slightly beige-orange coloured hydrochloride of bis(aminomethyl)phosphinic acid. One recrystallisation from water/acetone, water/ethanol or water alone, yields pure white crystalline product, which turns dark at 290° C. and melts at 307° C. with decomposition. The hydrochloride is insoluble in ethanol, acetone etc.

Analysis: $C_2H_9N_2O_2P.HCl$(160.54). Calculated: C 14.96; H, 6.28; N, 17.45; Cl, 22.08; P, 19.3%. Found: C, 15.05; H, 6.21; N, 17.04; Cl, 21.26; P, 19.09%.

Titration in water with 0.1N tetramethylammonium hydroxide gives a potential break: equiv. wt.: found 82 (calc. for 2 equivalents=80.27). In the titration with, e.g., NaOH, different salt forms of (I) result, to which the strong pH dependence of the $^{31}P$-chemical displacement also points. The pure hydrochloride of the formula

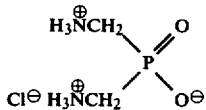

has a pH of about 5 when dissolved in water and a $^{31}$P-chemical displacement of −20.3 ppm. At pH 8, the betain

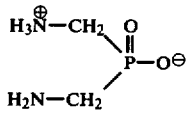

seems to be present, and at pH 9 the sodium salt

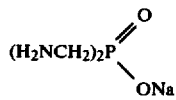

forms.

(2.) In another batch, 143 g of the hydrochloride of bis (benzylaminomethyl)phosphinic acid are dissolved in 3.5 liters of 70% acetic acid. To the solution are added 14 g of catalyst (5% palladium on carbon) and hydrogenation is effected with hydrogen under normal pressure and at 30°–35° C. After 14 hours, 108% of hydrogen has been taken up. The entire hydrogenation solution is then filtered and the clear, colourless filtrate concentrated by rotary evaporation. The residue is dried in vacuo, affording 64 g (95%) of white, crystalline end product with a melting point of 297° C. (with decomp.). The hydrochloride is dissolved in 120 ml of hot water, activated carbon is added, and the batch is stirred for 1 hour at 100° C. and filtered. On cooling, 1 part of pure hydrochloride of bis(aminomethyl)phosphonic acid crystallises out. Further pure end product is obtained from the mother liquor by addition of ethanol, so that the total yield amounts to 58.9 g (87.4%).

EXAMPLE 2

(a) Hydrochloride of bis(tert-butylaminomethyl)phosphinic acid (III)

With stirring, 81.5 g (0.5 mole) of bis(chloromethyl)-phosphinic acid $$(ClCH_2)_2P(O)OH$$

are slowly added to 366 g (500 ml, 5 moles) of tert-butylamine (see Example 1b). After the strongly exothermic reaction has subsided, the mixture is heated in a stirring autoclave for 12 hours to 120°–125° C. Excess tert-butylamine is distilled off from the resulting slightly yellow suspension, yielding 200.6 g of yellow solid as residue. As a preliminary experiment shows that all the chloromethyl groups have not yet been reacted, the yellow solid is again heated in the autoclave for 12 hours to 120°–125° C. Excess tert-butylamine is then distilled off and the residue is dissolved in hot ethanol. To this solution is added a solution of 100 NaOH in ethanol. Precipitated NaCl is then filtered off and the filtrate is concentrated. The residue is then dissolved again in hot ethanol (A) and 16.9 g remain undissolved (B).

Part A is acidified with conc. HCl, precipitated NaCl is filtered off and the slightly yellow coloured filtrate is concentrated. The residue is extracted several times with hot alcohol. On standing overnight, 19.9 g of white crystals (m.p. 260°–262° C., with decomp.) precipitate from the alcohol extracts. These crystals are the desired hydrochloride, (t-C$_4$H$_9$NHCH$_2$)$_2$POOH.HCl. A further 21.6 g of hydrochloride are obtained by concentrating the mother liquor, so that the total yield is 41.5 g (30.4%).

Analysis: [(CH$_3$)$_3$CNHCH$_2$]$_2$P(O)OH.1,5HCl C$_{10}$H$_{25}$N$_2$O$_2$P.1,5HCl (291.46). Found: C, 39.50; H, 9.8; N, 9.4; Cl, 18.2; P, 10.5%. Calculated: C, 41.21; H, 9.1; N, 9.1; Cl, 18.4; P, 10.6%;

(b) Hydrobromide of bis(aminomethyl)phosphinic acid 5.45 g (0.02 mole) of the above hydrochloride are heated with 20 ml of HBr (48% in H$_2$O) for 24 hours to 175° C. in a bomb tube. After cooling to room temperature, two phases are present. The upper phase consists of hydrocarbons. From the lower phase, 1.53 g (37.3%) of the desired hydrobromide of bis(aminomethyl)phosphinic acid crystallise. Melting point: 260–267° C. (with decomp.).

Sodium bis(aminomethyl)phosphinate,

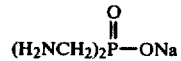

20.06 g of hydrochloride (H$_2$NCH$_2$)$_2$P(O)OH.HCl (0.125 mole) are dissolved in 150 ml of water and to this solution is slowly added a solution of 10 g (0.250 mole) of NaOH in 100 ml of water. After stirring for 1 hour, the mixture is concentrated to dryness and the residue is extracted twice hot with ethanol. Evaporation of the combined ethanol extracts yields 17.1 g (93.7%) of sodium salt as a white powder which sinters at 160° C., becomes wax-like at 190° C., and decomposes at 210° C. with formation of gas.

C$_2$H$_8$N$_2$O$_2$PNa(146.06). Calculated: C, 16.4; H, 5.52; N, 19.18; P, 21.21, Na, 15.7%. Found: C, 15.6; H, 5.4; H, 17.7; P, 19.8; Na, 16.3%.

Free bis(aminomethyl)phosphinic acid,

With stirring, 0.4% g of NaOH, dissolved in 20 ml of H$_2$O, is added to 2 g of hydrochloride

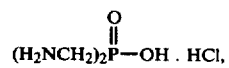

dissolved in H$_2$O. The mixture is then concentrated to dryness and the residue is extracted with ethanol. After the alcohol has been evaporated off, free bis(aminomethyl)phosphinic acid is obtained in quantitative yield as a white powder with a melting point of 107.5°–122° C. On further heating it remains wax-like and at 160° C. begins to decompose with formation of gas.

The free acid and the salts thereof possess plant growth-regulating, especially inhibiting, properties.

As already mentioned, the salts of the new acid (I) and the use thereof as plant grown regulators constitute the object of the present invention.

In addition to acid addition salts with strong acids which are tolerated by plant physiology (HCl, HBr, etc.), it will be understood that mention is also to be made of the alkali metal and alkaline earth metal salts, iron salts, etc., the salts of organic amines, of protonated and quaternary nitrogen bases, in principle all cations which are tolerated by plant physiology, including those which themselves possess growth inhibiting properties.

The invention also relates to a composition for and method of inhibiting the growth of mono- and dicotyledonous plants, especially grasses and cereal crops, soya and ornamentals.

A method of inhibiting plant growth is to be understood as meaning a control of natural plant development which effects a slowing down of this process. By means of such a method it is possible to bring about artificially retarding phases in the plant development (growth in length, sucker formation, new growth, blossoming, fruit setting, etc.). The method of growth regulation is applied at a period of plant development to be determined in each individual case. The new acid of the formula I and the salts thereof can be applied before or after the emergence of the plants, for example to the seeds or seedlings, to roots, tubers, stems, leaves, blossoms or other parts of plants, for example by applying the active compound itself or in the form of a composition to the plants and/or by treating the nutrient medium of the plant (soil).

The primary effect attained by the new active substances consists in the desired reduction of the plant size, in particular of the growth in height. In general, a certain change in the form of the plant is allied to this reduction in size. As a direct consequence of the reduction of the growth in height the plant is strengthened: leaves and stems are better developed. By shortening the distance between internodes in monocotyledonous plants the breaking strength is increased. In this way it is possible to prevent to a great extent harvest losses caused by thunderstorms, prolonged rainfall, etc., which usually result in a lodging of crops of cereals and leguminous plants, and thereby to facilitate harvesting. As side-effect, the reduced growth in height of useful plants results in a saving of fertilisers. This also applies equally to ornamental plants and ornamental grass plots, turf for sporting activities, grass-covered open spaces, etc.

A much greater problem posed by pure grass cultivations, however, is the actual cutting of the grass itself, whether in open spaces of urban areas, industrial sites, playing fields, along main roads, on railway embankments or the embankments of water bodies. In all these cases it is necessary to cut the turf or grass periodically. This operation is not only time-consuming, complicated and expensive in respect of labour and machinery, but involves the personnel concerned and traffic users in considerable hazard.

For this reason there is an urgent need in areas with extensive traffic networks to maintain and tend the grassy covering for strengthening road shoulders and embankments on traffic routes on the one hand, and on the other to keep it at a reasonable height by simple means during the entire vegetation period. This need is fulfilled in a very advantageous manner by applying bis(aminomethyl)phosphinic acid or one of the salts thereof.

The active substances of the present invention thus intervene in the physiological processes of plant growth and are therefore growth regulators which have a growth retarding effect.

The different inhibiting effects depend substantially on the time of application, referred to the development stage of the plant, and on the concentrations employed. Accordingly, growth inhibitors can also bring about that the nutrients are beneficial to the flower and fruit formation, whereas the vegetative growth is restricted.

The active substances are usually applied in the form of compositions, i.e., after the addition of carriers and other ingredients.

Such compositions are prepared in a manner which is known per se by intimately mixing and grinding the acid (I) or one of the salts thereof with solid or liquid carriers and additives which are conventionally used in the art of formulation, for example natural or regenerated substances, solvents, dispersants, wetting agents, tackifiers, thickeners and binders.

The conventionally prepared compositions can thus be processed to the following formulations:
solid formulations:
  dusts, tracking powders and granules (coated granules, impregnated granules and homogenous granules).
liquid formulations:
  (a) active substances which are dispersable in water: wettable powders, pastes and emulsions;
  (b) solutions.

Biological Tests in Support of the Growth Inhibition

Growth inhibition in grasses

Seeds of the grasses *Lolium perenne, Poa pratensis, Festuca ovina,* and *Dactylis glomerata* were sown in plastic dishes filled with an earth/turf/sand mixture (6:3:1). The emergent grasses were cut back weekly to a height of 4 cm above the soil and 1 day after the last cut were sprayed with aqueous spray broths of an active substance of the formula I. The amount of active substance corresponded to a rate of application of 5 kg of active substance per hectare. The growth of the grasses was evaluated 10 and 27 days after application. The hydrochloride of bis(aminomethyl)phosphinic acid effected a pronounced growth inhibition to 10 to 25% of the normal growth in height, depending on the species of grass and referred to untreated controls.

Growth inhibition in cereals

Spring wheat (*Triticum aestivum*), summer barley (*Hordeum vulgare*) and rye (Secale) was sown in sterilised soil in plastic beakers and reared in a greenhouse. The cereal shoots were treated 5 days after sowing with a spray broth of the active substance. The leaf application corresponded to 6 kg of active substance per hectare. Evaluation after 21 days showed that the hydrochloride of bis(aminomethyl)phosphinic acid effected a 10 to 50% shortening of the stalk, depending on the species of cereal and referred to untreated control plants.

What is claimed is:

1. Bis(aminomethyl)phosphinic-acid of the formula I

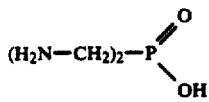

and the salts thereof with strong acids as well as the salts thereof with metallic bases, amines, ammonia and quaternary ammonium bases.

2. A composition for the regulation of plant growth, especially for the inhibition thereof, which contains as active ingredient an effective amount of bis(aminomethyl)phosphinic acid of formula I as claimed in claim 1 or of a salt thereof.

3. A method for retarding plant growth which comprises treating areas with plants whose growth is to be retarded with an effective amount of bis(aminomethyl)phosphinic acid of formula I as claimed in claim 1 or of a salt thereof.

4. A method according to claim 3 which comprises retarding the growth of grasses and cereal crops.